United States Patent [19]

Moxham

[11] 4,330,676

[45] May 18, 1982

[54] OXIDATION PROCESS

[75] Inventor: Peter H. Moxham, Middlesbrough, England

[73] Assignee: Imperial Chemical Industries Limited, London, England

[21] Appl. No.: 918,266

[22] Filed: Jun. 22, 1978

[30] Foreign Application Priority Data

Jul. 4, 1977 [GB] United Kingdom ............... 27887/77

[51] Int. Cl.$^3$ ........................................... C07C 51/16
[52] U.S. Cl. ..................................... 562/416; 562/421
[58] Field of Search ............... 260/525, 524 R, 523 R; 562/416, 421

[56] References Cited

U.S. PATENT DOCUMENTS 3,853,924 12/1974 Meyer et al. ......................... 260/525

Primary Examiner—Alan Siegel
Attorney, Agent, or Firm—Cushman, Darby & Cushman

[57] ABSTRACT

A reaction slurry of a solid aromatic carboxylic acid such as terephthalic acid in mother liquor such as acetic acid which has been obtained by catalytic oxidation of an aromatic compound such as p-xylene in a solvent such as acetic acid is held in a washing zone to allow the solid acid to separate under gravity into fresh solvent, and a washed slurry of solid acid in solvent is withdrawn.

17 Claims, 1 Drawing Figure

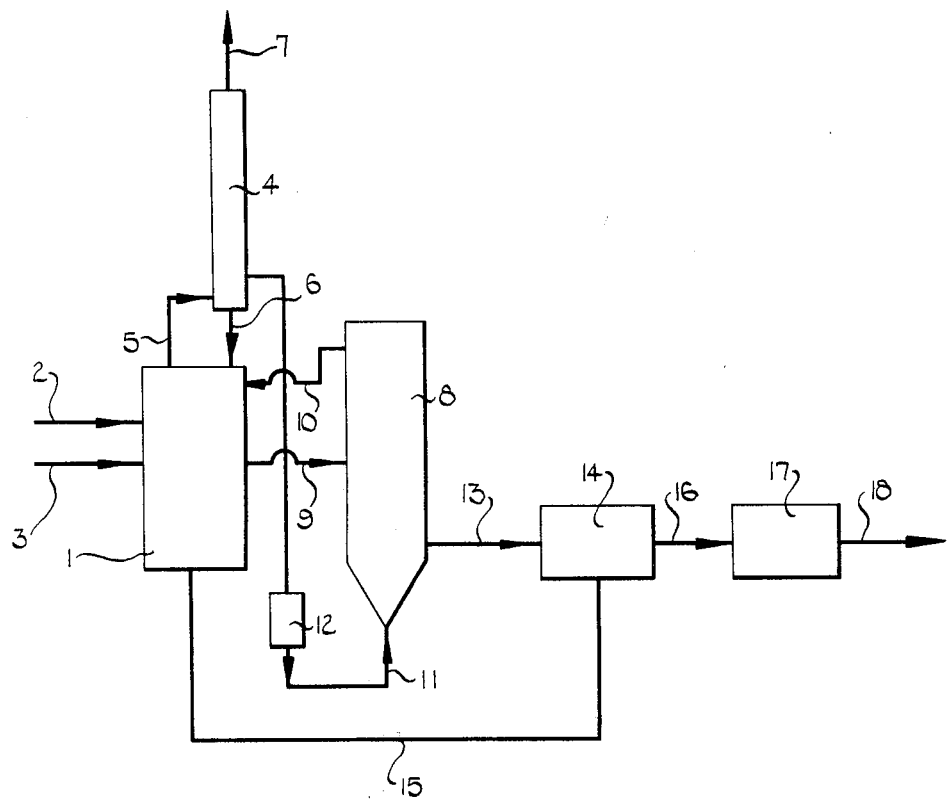

OXIDATION PROCESS

This invention relates to a process for the oxidation of substituted aromatic compounds to aromatic carboxylic acids.

It is already known to oxidise certain substituted aromatic compounds to aromatic carboxylic acids, for example p-xylene to terephthalic acid, by means of oxygen or a molecular oxygen-containing gas in a solvent in the liquid phase in presence of a heavy metal oxidation catalyst. Such oxidation results in a slurry of the solid aromatic carboxylic acid in a mother liquor comprising the said solvent, and separation of the solid from the mother liquor is then effected by conventional separation methods such as filtration or centrifuging to give a filter cake or centrifuge cake. It is then necessary in the majority of cases to remove the remaining mother liquor in the cake by washing the cake on the filter or centrifuge, for example with fresh solvent, or by reslurrying the cake with, for example, fresh solvent and then effecting a second separation.

We have now found that in oxidation processes such as those mentioned the mother liquor may be removed from the solid aromatic carboxylic acid, prior to isolating the solid, by a special washing procedure, thereby eliminating the necessity for washing filter cake or centrifuge cake, or carrying out a reslurrying and second separation operation. At the same time the particle size of the solid aromatic carboxylic acid may be controlled by eliminating undesired fine material, and the purity of the isolated aromatic carboxylic acid may be improved.

According to our invention we provide a continuous process for the oxidation of an aromatic compound substituted by at least one alkyl, hydroxyalkyl or formyl group to an aromatic carboxylic acid, which process comprises introducing into a reaction zone the said substituted aromatic compound, a solvent, a heavy metal oxidation catalyst and oxygen or a molecular oxygen-containing gas, maintaining the resulting mixture in the reaction zone at a temperature and pressure at which the said oxidation reaction is effected in the liquid phase to produce a reaction slurry of solid said aromatic acid in mother liquor comprising said solvent, holding said reaction slurry in a washing zone to allow solid said aromatic acid to separate under gravity from said mother liquor into fresh said solvent fed to the bottom of the washing zone and withdrawing from said washing zone a washed slurry of solid said aromatic acid in said solvent.

The aromatic compounds to be oxidised by the process of our invention are substituted by alkyl, hydroxyalkyl or formyl groups. Particularly suitable alkyl groups are methyl, ethyl and isopropyl groups; particularly suitable hydroxyalkyl groups are hydroxymethyl and hydroxyethyl groups. One, two or more such groups may be present in the aromatic nucleus and the groups may be the same or different. The aromatic nucleus may, for example, be a benzene or naphthalene nucleus. Particularly suitable compounds to be oxidised are toluene, ethylbenzene, isopropylbenzene, o-, m- and p-xylene, cumene, pseudocumene, the isomeric diisopropylbenzenes, durene, mesitylene, hydroxymethylbenzene, hydroxyethylbenzene, bis-hydroxymethylbenzenes, benzaldehyde, the isomeric tolualdehydes and 2,6-dimethyl-naphthalene. Suitable aromatic compounds also include those which are already partially oxidised to carboxylic acids and their corresponding esters, for example p-toluic acid, methyl p-toluate and p-carboxybenzaldehyde. The process of our invention is particularly suitable for the oxidation of p-xylene to terephthalic acid.

The solvent used in the process of our invention is a solvent for the aromatic compound to be oxidised. The solvent should be substantially unaffected under the oxidation conditions. Particularly suitable solvents are carboxylic acids, especially lower aliphatic mono-carboxylic acids having from 2 to 8 carbon atoms and benzoic acid. Acetic acid is a preferred solvent. Water may also be used as a solvent.

The heavy metals used as catalysts include vanadium, chromium, manganese, iron, cobalt, nickel, molybdenum, cerium and zirconium. Particularly suitable is cobalt especially in combination with manganese and possibly also with cerium or zirconium. The heavy metals are used, for example, in the form of their inorganic or organic acid salts especially the bromides or acetates. The catalyst may be used in conjunction with an oxidation promoter, for example an aldehyde or ketone such as acetaldehyde or methyl ethyl ketone, or especially, a source of bromine e.g. a bromide. Suitable bromides are, for example, bromides of the heavy metals used, for example cobalt or manganese bromides, alkali metal or ammonium bromides or hydrobromic acid. Bromine itself, or organic bromo compounds such as tetrabromoethane may also be used as the source of bromine.

The molecular oxygen-containing gas used in our process is conveniently air, but mixtures of oxygen and nitrogen with a higher or lower oxygen content than that of air may also be used. Pure oxygen may, of course, be used.

The oxidation may be effected, for example, at temperatures in the range 80° to 270° C. Pressures are at least such that a liquid phase is maintained in the reactor, and are, for example, within the range of 1 to 50 bar. Suitable processes for the oxidation in this manner of p-dialkybenzenes, especially p-xylene to terephthalic acid, are described, for example, in British Pat. Nos. 786,930, 807,091, 833,438, 841,425 and 1,062,482 and U.S. Pat. No. 3,089,907. A particularly suitable and economic method for oxidising p-xylene to terephthalic acid suitable, without a special catalytic hydrogenation purification treatment, for use in the direct esterification of ethylene glycol in the manufacture of polyethylene terephthalate is described and claimed in our British Pat. No. 1511181 (equivalent Belgian Pat. No. 840,624).

The oxidation reaction may be effected in more than one stage, and the reaction mixture may be subjected to a post-oxidation treatment in a separate vessel in order to ensure completion of the oxidation.

The reaction slurry of aromatic carboxylic acid in mother liquor resulting from the oxidation reaction is passed from the reaction zone to the washing zone which is preferably substantially vertically disposed and is preferably elongated in the vertical direction to minimise back-mixing of mother liquor with solvent. The washing zone is filled with liquid and is fed with fresh liquid solvent introduced at the bottom of the zone. The particles of aromatic carboxylic acid fall down the column of liquid in the washing zone under the influence of gravity, the larger particles falling faster than the finer ones. A slurry of aromatic carboxylic acid particles in liquid solvent is withdrawn from a lower region of the washing zone, the feed of solvent to the bottom of the zone being at least sufficient to supply the liquid for the withdrawn slurry. The mother liquor from which the aromatic carboxylic acid settles out may be withdrawn from an upper region of the washing zone.

The feed of fresh solvent to the bottom of the washing zone is preferably greater than that which is just sufficient to supply the liquid for the withdrawn slurry. With a greater feed than this minimum there is an upward flow of fresh solvent in the washing zone and this assists in displacing mother liquor from the particles of aromatic carboxylic acid, which is already effected to some degree by the downward settling of such particles under gravity. The upward flow of solvent also assists in segregating the finer particles of aromatic carboxylic acid from the larger, and may be adjusted to ensure that the finer particles which are generally undesired are carried upwards in the washing zone with the mother liquor and are withdrawn with it from an upper region of the washing zone.

The upward flow of solvent, by weight, in the washing zone is, for example, from zero to 20 times the rate at which aromatic carboxylic acid is withdrawn from the washing zone, and is preferably from 1 to 3 times.

Preferably at least a part of any mother liquor withdrawn from an upper region of the washing zone is recycled to the reaction zone. A part of this mother liquor may be taken as a purge, which may be rejected, or may be treated to remove impurities before recycle to the reaction zone, or may be treated to recover catalyst values which may be recycled to the reaction zone. Alternatively, however, a purge may be taken of the reaction slurry from the reactor.

The fine particles of aromatic carboxylic acid which may be present in any recycled mother liquor usually contain a higher proportion of impurities than the coarser particles. Since these impurities are, at least in part, incompletely oxidised reaction intermediates, recycling them for further oxidation can result in a higher overall yield of product. In the case of the oxidation of p-xylene to terephthalic acid, such reaction intermediates are, for example, p-toluic acid and p-carboxybenzaldehyde.

The washed slurry of aromatic carboxylic acid with solvent which is withdrawn from a lower region of the washing zone is preferably subjected to a solid/liquid separation treatment, for example filtration or centrifuging to separate the aromatic carboxylic acid from the solvent. The aromatic carboxylic acid may then be dried.

The temperature of the fresh solvent fed to the bottom of the washing zone may vary over a wide range. On the one hand, for example, the temperature may be equal to or close to that of the reaction slurry passing to the washing zone from the reaction zone. This will help to ensure that there is no secondary precipitation of aromatic carboxylic acid which could result in the formation of an unduly high proportion of fine particles with a higher impurity level and thus to a product of inferior quality. On the other hand the temperature of the solvent may be significantly below that of the reaction slurry so as to effect cooling of the aromatic carboxylic acid and ensure that when the said aromatic acid is separated from the solvent the temperature is below the boiling point of the latter at atmospheric pressure, so avoiding the necessity for pressure equipment at the separation stage or the use of a separate intermediate cooling stage. In this case the upward flow of fresh solvent in the washing zone may be adjusted to ensure that any fine particles of aromatic carboxylic acid formed are recycled to the reaction zone. The higher density of the cooler solvent compared with that of the mother liquor helps to prevent back-mixing of solvent with mother liquor. However, it is preferable that the temperature of the solvent feed to the washing zone be as high as possible consistent with separation at atmospheric pressure, for example in the case of acetic acid as solvent the temperature is, for example, in the range 100° to 110° C.

The feeding and recycle of solvent in the system comprising the reaction zone and the washing zone may be arranged to ensure efficient use of solvent and conservation of energy. In the oxidation it is customary to allow the solvent to reflux from a condenser above the reaction zone. Since water is formed in the oxidation reaction, and it is generally undesirable to allow the concentration of water in the reaction mixture to become too great, a proportion of the condensed liquid, which contains solvent and water, may be withdrawn to control the water concentration. Such condensed liquid, preferably after treatment in, for example, a dehydrating still to remove at least a part of the water, may be used as feed to the washing zone.

In a more energetically efficient process, however, a fractionating column may be arranged above the reaction zone to receive the vapours therefrom. The column may be operated so that most of the water leaves the top of the column as vapour, condensed solvent is returned from the bottom of the column to the reaction zone, and a side stream of solvent is withdrawn from the column to serve as feed to the washing zone, if required after prior cooling.

Although acetic acid is our preferred solvent, the process of our invention is of particular value when using benzoic acid as solvent, which, being a solid at the ordinary temperature (m.p. 122° C), sometimes gives difficulties owing to the ease of solidification and the difficulty of separating from a different aromatic carboxylic acid product of oxidation. These difficulties are much less significant when benzoic acid is used as solvent in our process, and benzoic acid has the advantage of great resistance to oxidation and ease of separation from water. Thus when a column is used above the reaction zone for removing water of reaction a much smaller number of trays is needed for benzoic acid as solvent than for acetic acid.

The reaction zone is conveniently contained within a suitable pressure reactor, made of corrosion-resistant material on account of the carboxylic acid solvent used. Where the catalyst contains a bromide a material must be used capable of withstanding the resulting highly corrosive reaction mixture, for example titanium, but in the absence of bromide less expensive materials such as stainless steel are suitable. The reactor is preferably agitated. The washing zone is conveniently contained within a vertical column which is corrosion-resistant and capable of withstanding pressure. Where a bromide is present it is only the upper part of the column that is in contact with bromide and need be constructed of expensive corrosion-resistant material such as titanium. It is an advantage of our process that the items of plant that need to be constructed of expensive bromide-resistant materials are limited: for example, the separation equipment such as centrifuges need not be so constructed.

The vessel containing the washing zone may be separate from that containing the reaction zone or integral with it. Where the vessels are separate the slurry of aromatic carboxylic acid in mother liquor is passed from the reaction zone to an upper region of the washing zone preferably below the top; and the mother liquor is withdrawn preferably from the top of the washing zone or at least at a point above the feedpoint of reaction slurry. Where the vessels are integral, the washing zone is placed below the reaction zone.

Where separate vessels are used they may operate at somewhat different pressures, for example a higher pressure in the reactor vessel will ensure flow of reactor slurry to the washing vessel. In this case, however, where mother liquor is recycled, it will be necessary to use forced circulation, e.g. by means of a pump, for this purpose.

In order to ensure regular flow of fresh solvent in the washing vessel, it may have a generally conically shaped bottom, or the solvent may be fed through, for example, a distributor arranged to ensure such regular flow.

The efficiency of the washing operation may be varied at will depending on the quality of the isolated aromatic carboxylic acid it is desired to achieve. The operation may involve not only separation of mother liquor from solid aromatic carboxylic acid, but possibly also desorption of impurities from the solid acid and/or recrystallisation of the solid acid. The efficiency of the operation will depend on the amount of fresh solvent used in relation to the output of aromatic carboxylic acid from the reactor, on the concentration of the slurry of aromatic carboxylic acid in fresh solvent which is withdrawn, and on the residence time of the solid acid in the fresh solvent. These factors will determine the size and shape of the washing vessel in relation to that of the reaction vessel. The residence time may, for example, vary from 10 minutes to 2 hours or more.

The invention may be illustrated by reference to the accompanying drawing which is a flow diagram described with reference to the manufacture of terephthalic acid from p-xylene.

In the drawing, 1 is a reactor and 2 and 3 are conduits for the introduction of p-xylene and air respectively into the reactor, 4 is a fractionating column, 5 is a conduit for passing gases and vapours effluent from the reactor to the column, 6 is a conduit for returning condensed liquid to the reactor and 7 is a vent for water vapour and non-condensible gases leaving the column, 8 is a wash vessel, 9 is a conduit for feeding reaction slurry from the reactor to the wash vessel and 10 is a conduit for returning mother liquor from an upper region of the wash vessel to the reactor, 11 is a conduit for feeding a liquid solvent side stream from the column 4 to the bottom of the wash vessel via a cooler 12, (which is optional), 13 is a conduit for feeding a slurry of terephthalic acid and solvent from the wash vessel to a centrifuge 14, and 15 is a conduit for conveying solvent from the centrifuge to the reactor, 16 is a conveyor for conveying the centrifuged terephthalic acid to a dryer 17 and 18 is a conveyor for carrying dried terephthalic acid to storage.

In continuous operation p-xylene and air are fed to the reactor which contains solvent and catalyst maintained at the appropriate reaction temperature. Solvent is refluxed from the column 4 and water of reaction is removed from the top of the column. A slurry of terephthalic acid in reaction mother liquor is fed from the reactor to the wash vessel where it contacts fresh solvent fed to the bottom of the vessel from a side stream of the column 4 via conduit 11. A slurry of terephthalic acid in fresh solvent is fed from the wash vessel to the centrifuge whence the separated solvent is fed to the reactor and the separated solid terephthalic acid is conveyed to the dryer. The displaced mother liquor, free of all but fine particles of terephthalic acid, is returned from the top of the column to the reactor via conduit 10.

The terephthalic acid obtained by our process may, if necessary, be purified by known procedures, for example by catalytic hydrogenation in aqueous solution at high temperature followed by crystallisation as described, for example, in British Pat. No. 994,769. Where appropriate oxidation conditions are chosen, however, such special purification may be unnecessary. For example where, as previously mentioned, the oxidation conditions described and claimed in our British Pat. No. 1511181 are employed the product of our process is suitable, without such special purification, for use in the direct esterification of ethylene glycol in the manufacture of polyethylene terephthalate suitable for conversion into fibres.

Advantages of our process are that the separation of fine particles of aromatic carboxylic acid by secondary crystallisation, or the separation of solid impurities, during conventional separation of the solid aromatic carboxylic acid from the mother liquor is avoided, because in our process the mother liquor is displaced by fresh solvent; and, as already mentioned, this also reduces the number of separators required. Moreover, fine particles already present in the mother liquor are separated from the coarser particles and recycled to the reactor. In this way filtration difficulties due to fine particles are avoided and a product of more uniform particle size is obtained leading to greater ease in powder handling. It is therefore unnecessary, as described in the prior art, for example in British Pat. No. 970,491, to control particle size by the use of a succession of crystallisers in series. Again, as already mentioned, the amount of equipment to be made of special corrosion-resistant materials when using bromide-containing catalysts is reduced. Further, our process enables a high degree of recycle of mother liquor to be achieved with consequent increase in yield and reduction in operating costs.

I claim:

1. A continuous process for the oxidation of an aromatic compound substituted by at least one alkyl, hydroxyalkyl or formyl group to an aromatic carboxylic acid which comprises introducing into a reaction zone the substituted aromatic compound, a solvent, a heavy metal oxidation catalyst and oxygen or a molecular oxygen-containing gas, maintaining the resulting mixture in the reaction zone at a temperature and pressure at which the said oxidation reaction is effected in the liquid phase to produce a reaction slurry of solid said aromatic acid in mother liquor comprising said solvent, holding said reaction slurry in a washing zone to allow solid said aromatic acid to separate under gravity from said mother liquor into fresh said solvent fed to the bottom of the washing zone and withdrawing from said washing zone a washed slurry of solid said aromatic acid in said solvent, in which said washing zone is substantially vertically disposed and is elongated in the vertical direction and the feed of fresh solvent to the bottom of the washing zone is greater than that which is just sufficient to supply the liquor for the withdrawn slurry, mother liquor from which the aromatic carboxylic acid settles out being withdrawn from an upper region of the washing zone.

2. A process according to claim 1 in which the aromatic compound comprises a benzene or naphthalene nucleus substituted by one, two or more methyl, ethyl, isopropyl, hydroxymethyl or hydroxymethyl groups or is an aromatic compound which is already partially oxidised to a carboxylic acid or its corresponding ester.

3. A process according to claim 1 in which the solvent is a carboxylic acid or water.

4. A process according to claim 1 in which the heavy metal oxidation catalyst comprises vanadium, chromium, manganese, iron, cobalt, nickel, molybdenum, cerium or zirconium, and wherein there is an upward flow of fresh solvent in said washing zone.

5. A process according to claim 1 in which the heavy metals are used in the form of their inorganic or organic acid salts.

6. A process according to claim 1 in which the heavy metal oxidation catalyst is used in conjunction with an oxidation promoter.

7. A process according to claim 6 in which the promoter is an aldehyde, a ketone, or a source of bromine.

8. A process according to claim 1 in which the upward flow of solvent, by weight, in the washing zone is from zero to 20 times the rate at which aromatic carboxylic acid is withdrawn from the washing zone.

9. A process according to claim 8 in which the upward flow is 1 to 3 times the rate at which aromatic carboxylic acid is withdrawn from the washing zone.

10. A process according to claim 1 in which at least a part of any mother liquor withdrawn from an upper region of the washing zone is recycled to the reaction zone.

11. A process according to claim 1 in which a purge is taken either from the mother liquor withdrawn from an upper region of the washing zone or from the reaction slurry from the reactor.

12. A process according to claim 1 in which the temperature of the fresh solvent fed to the bottom of the washing zone is as high as possible consistent with separation of aromatic acid from solvent at atmospheric pressure.

13. A process according to claim 12 in which the solvent is acetic acid and the temperature of the fresh solvent is 100° to 110° C.

14. A process according to claim 1 in which solvent fed to the washing zone is liquid condensed from the reaction zone which has been treated to remove at least part of its water content.

15. A process according to claim 1 in which solvent fed to the washing zone is a side stream from a fractionating column arranged above the reaction zone and receiving vapours therefrom.

16. A process according to claim 1 in which the residence time of the solid aromatic carboxylic acid in the fresh solvent lies in the range 10 minutes to 2 hours.

17. A process according to claim 1 in which
(a) m- or p-xylene, p-toluic acid, methyl-p-toluate or p-carboxybenzaldehyde is continuously introduced into a reaction zone with a solvent which is a lower aliphatic mono-carboxylic acid having from 2 to 8 carbon atoms, benzoic acid or water, an oxidation catalyst which is cobalt and manganese in the form of their bromides or acetates and a heavy metal bromide, an alkali metal bromide, ammonium bromide, hydrogen bromide, bromine itself or an organo-bromine compound together with oxygen or a molecular oxygen-containing gas at 80° to 270° C. and 1 to 50 bar pressure so as to produce a reaction slurry of iso- or tere-phthalic acid in the mother liquor comprising said solvent,
(b) said reaction slurry is held in a washing zone to allow solid iso- or tere-phthalic acid to separate under gravity from said mother liquor into fresh solvent fed to the bottom of the washing zone and
(c) a washed slurry of iso- or tere-phthalic acid in said solvent is withdrawn from said washing zone.

* * * * *

UNITED STATES PATENT AND TRADEMARK OFFICE
CERTIFICATE OF CORRECTION

PATENT NO. : 4,330,676
DATED : May 18, 1982
INVENTOR(S) : Peter H. Moxham

It is certified that error appears in the above-identified patent and that said Letters Patent are hereby corrected as shown below:

IN THE CLAIMS

Claim 2, line 4, "hydroxymethyl" (second occurrence) should read --hydroxyethyl--

Signed and Sealed this

Tenth Day of August 1982

[SEAL]

Attest:

GERALD J. MOSSINGHOFF

Attesting Officer

Commissioner of Patents and Trademarks